United States Patent [19]
Dorsey, III

[11] Patent Number: 5,571,126
[45] Date of Patent: Nov. 5, 1996

[54] FAN SPRAY SURGICAL PROBE

[75] Inventor: James H. Dorsey, III, Delray Beach, Fla.

[73] Assignee: C.R. Bard, Inc., Murray Hill, N.J.

[21] Appl. No.: 294,088

[22] Filed: Aug. 22, 1994

[51] Int. Cl.⁶ .................................................. A61B 17/32
[52] U.S. Cl. ............................................. 606/167; 606/190
[58] Field of Search .................................... 606/167, 190; 604/22; 239/597, 599

[56] References Cited

U.S. PATENT DOCUMENTS 4,709,697  12/1987  Muller ..................................... 128/303
4,988,043   1/1991  Lechler .................................. 239/597
5,199,943   4/1993  Wypych .................................. 604/22

*Primary Examiner*—Michael Powell Buiz
*Assistant Examiner*—Mark S. Leonardo
*Attorney, Agent, or Firm*—Darby & Darby, P.C.

[57] ABSTRACT

A surgical probe is disclosed for use in defining and dissecting tissue planes. The operative end of the probe is defined to provide a flat wide fan-like shaped spray at the operative end which aids in lifting organs, such as the gall bladder, as well as loosening the adhesion underneath such organs. The probe can also be provided with a dissecting edge, also at the operative end of the probe. The dissecting edge can be used to cut and dissect the desired organ(s) of the patient.

20 Claims, 3 Drawing Sheets

FAN SPRAY SURGICAL PROBE

BACKGROUND OF THE INVENTION

1. Field of the Invention

The present invention relates generally to the field of laparoscopic and endoscopic surgery and in more particularly to a specially designed surgical irrigation probe tip configuration for defining an irrigation stream configuration which may also be used for stripping tissues of adhesive blood clots and dissecting tissue planes.

2. Description of the Prior Art

During laparoscopic surgery, a form of endoscopic surgery dealing specifically with the abdominal area, a surgeon typically makes several small, spaced incisions through the abdominal wall of an anesthetized patient. A source of compressed CO2 is then provided through one of the incisions to inflate the abdomen, thus raising the abdominal wall above the organs and intestines of the patient. A space is thereby created between the abdominal wall and organs/intestines which allows manipulation of surgical instruments which have been inserted into the abdomen through at least one of the other incisions.

One problem that frequently occurs during such surgeries is when removing or moving organs, such as the gall bladder, there is a layer of adhesion holding such organ in place. In the case of the gall bladder, the layer of adhesion helps to retain and allow the gall bladder to sit on the liver bed. Thus, when removing the gall bladder one must overcome this layer of adhesion.

What is needed in the art is a surgical instrument which can supply a high pressurized linear stream of fluid which is a thin flat spray therefore directing energy along the same plane as the adhesion to dissect the adhesion holding an organ, such as the gall bladder, and for subsequent removal of such organ. It is, therefore, to the effective resolution of the aforementioned problems and shortcomings that the present invention is directed.

SUMMARY OF THE INVENTION

The present invention relates to a surgical probe having a specially designed operative end which allows the probe to provide fluid, such as water, in a wide flat spray manner to cleanse tissue of blood and debris and which also may be used to dissect the hold provided by the layer of adhesion on the organ to keep such organ in place. Once the adhesion has been dissected, may be removed. Thus, the present invention aids in dissecting tissue planes, by defining and dissecting such tissue planes.

The tip of the present invention may be provided with a specifically designed blunt and sharp end. The sharp leading end is designed to actually mechanically separate tissues and allow the present invention to be inserted between two plains of tissue. The flat fan-like spray then dissects tissue along such plain.

A flat spray in abdominal laparascopic surgery acts very much like a paint stripper for blood and coagulated blood on tissues. In the past, a physician will direct pressurized irrigation around the target tissue in a very quick back and forth type motion. The present invention allows a user to very methodically and evenly cleanse surface tissues with a high pressure even spray that is more effective than a round, hose-like irrigation stream.

Irrigation splash back does not occur from using the present invention because the stream of irrigation is so thin. Nor will large drops splash back on the lens of a laparoscope and cloud the field of view as is common with the use of conventional probe tips. With the present invention the pressurized irrigation's energy is dissipated upon impact with tissue and irrigation bubbles up in a froth without any splash back.

The present invention can also be used as inner cannula which can be inserted through various outer probe tip cannulas.

Accordingly, it is an object of the present invention to provide a surgical probe for defining and dissecting tissue planes, as well as rinsing the abdominal cavity more thoroughly than was possible in the past.

It is another object of the present invention to provide a surgical probe which will provide a wide flat spray of fluid to a surgical site.

It is yet another object of the present invention to provide a surgical probe which will provide a wide flat spray of fluid to aid in dissecting adhesions within the abdominal region which hold a patient's organ, such as a gall bladder, in place.

It is even still another object of the present invention to provide a surgical probe which has a dissecting edge disposed at the operative end of such probe.

It is another object of the present invention to provide a surgical probe which will provide a wide flat spray of fluid to a surgical site and which can be inserted through various outer probe tip cannulas.

In accordance with these and other objects which will become apparent hereinafter, the instant invention will now be described with particular reference to the accompanying drawings.

BRIEF DESCRIPTION OF THE DRAWINGS

The invention may be better understood by reference to the drawings in which.

DESCRIPTION OF THE PREFERRED EMBODIMENTS

Figure 1:
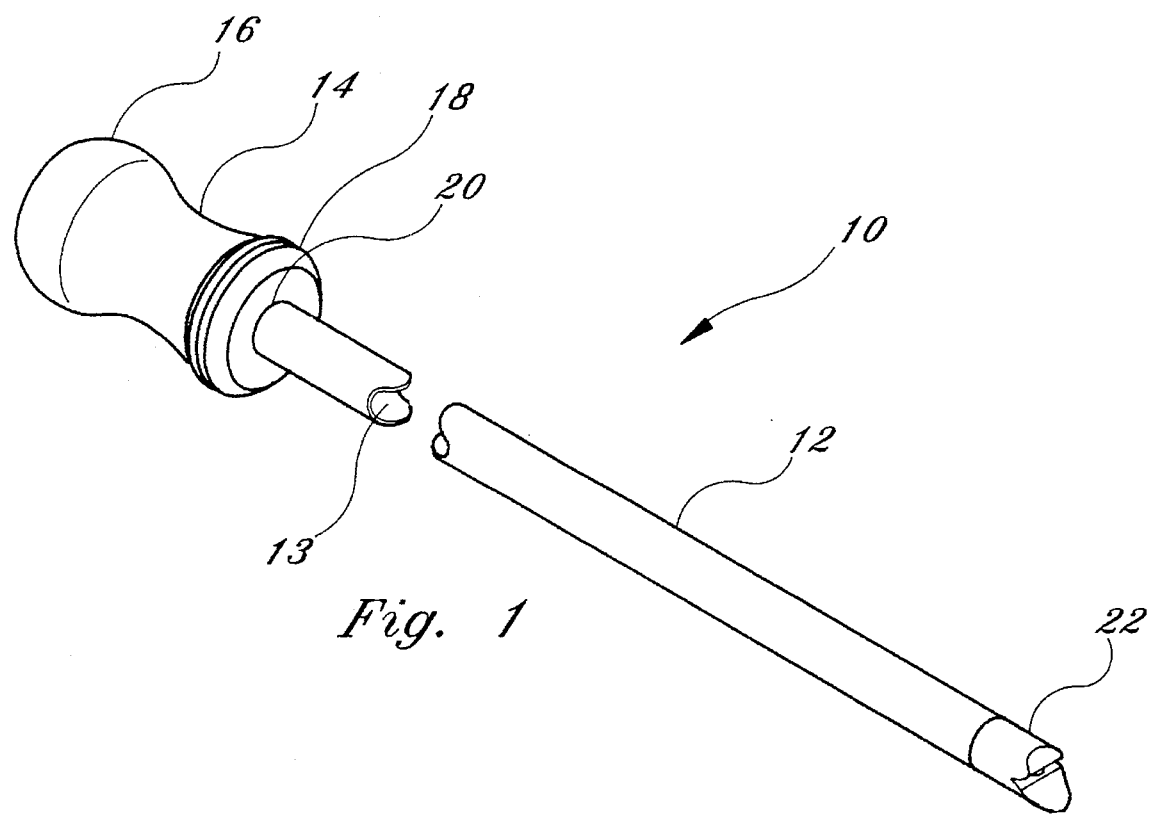
FIG. 1 is an isometric view of the present invention.

As seen in the drawing, the surgical probe of the present invention is generally shown at 10. Probe 10 includes a probe shaft 12 and a specially designed probe shaft housing or base 14. Shaft 12 includes a first end 20 and a second end 22. End 22 will also be referred throughout as operative member 22. Housing 14 includes a first end 16 and a second end 18. First end 16 can be attached to a trumpet valve as illustrated in U.S. Pat. No. 5,188,591 and my applications Ser. Nos. 07/989,109, now abandoned and 08/052,080 all of which are incorporated by reference herein. The as illustrated in U.S. Pat. No. , the trumpet valve can be attached to a source of fluid or irrigation. First end 16 may also be attached directly or indirectly by other conventional devices to other sources of fluid supply. Second end 18 encompasses a portion of first end 20 of shaft 12. Thus, housing 14 allows the internal passageway 13 extending throughout shaft 12 to communicate with the source of fluid supply, i.e. trumpet valve (not shown).

Figure 3:
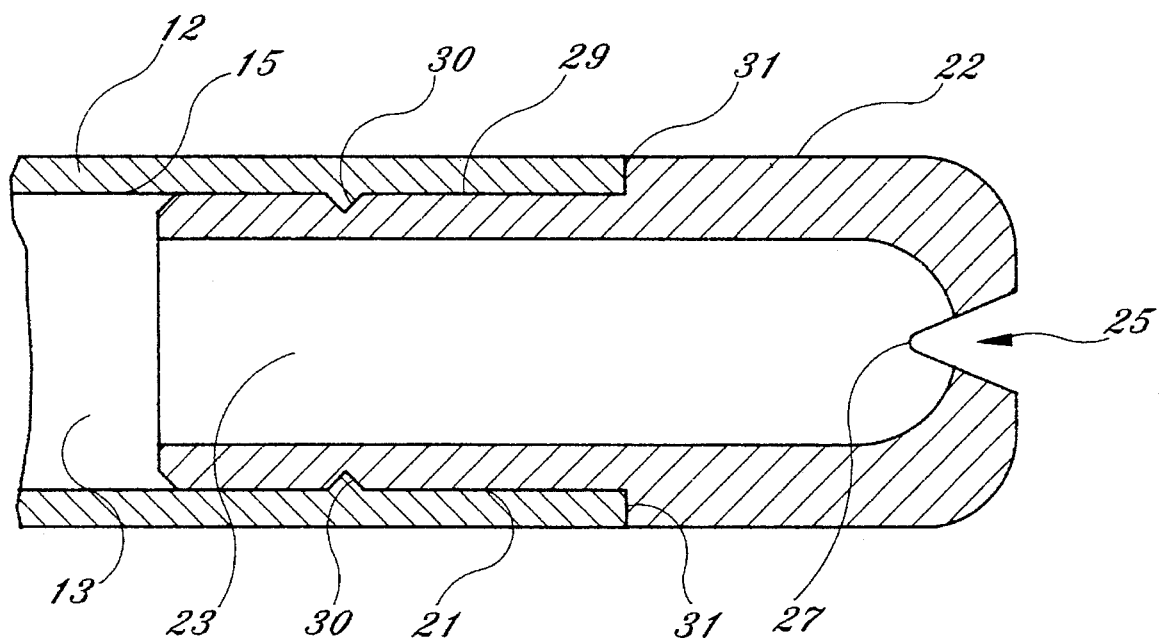
FIG. 3 is a sectional view of the operative end of the present invention.

As best seen in FIG. 3, the operative member 22 is shown attached to shaft 12 by notch and corresponding groove combination 30. In one embodiment, the notch is disposed on inner wall 15 of shaft 12, while the corresponding groove is disposed within the outer wall 29 of operative member 22. However, these positions may be reversed and the groove would thus be within inner wall 15 and the notch disposed along outer wall of operative member 22. Other connection methods which are well known in the art, such as welding, may be utilized for attaching operative member 22 to shaft 12.

Operative member 22 has a connection portion 21 which is inserted within internal passageway 13, until the notch is disposed within groove of combination 30, for attachment of end 22 to shaft 12. Accordingly, the outer diameter of connection portion 21 must be smaller than the diameter of internal passageway 13 of shaft 12. Once operative member 22 has been attached to shaft 12, this relationship is permanent and for all intents and purposes forming a one piece probe shaft with a specialized second end.

The outer wall 29 of operative member 22 defines an internal passageway 23 extended from the first end to the second end of operative member 22. Internal passageway is formed by creating a drilling round cutout within operative member 22. Internal passageway 23 communicates with internal passageway 13 of shaft 12, when operative member 22 is attached to shaft 12 as described above. As seen in FIG. 3, the diameter of passageway 23 is smaller than internal shaft passageway 13. Thus, fluid traveling through passageway 13, upon reaching passageway 13 will be restricted in volume. As such, the velocity of the fluid traveling through passageway 23 will increase as compared to the velocity of the fluid traveling through passageway 13 causing the fluid to shoot out of opening 25. The fluid is forced through opening 25 by the relatively small size of the hole at the end of passageway 23 (tip portion of cutout 27) along with the shape of cutout 27. V-shape cutout 27 causes the fluid to shoot out of opening 25 in a relatively flat wide fan-like shaped spray.

Figure 2:
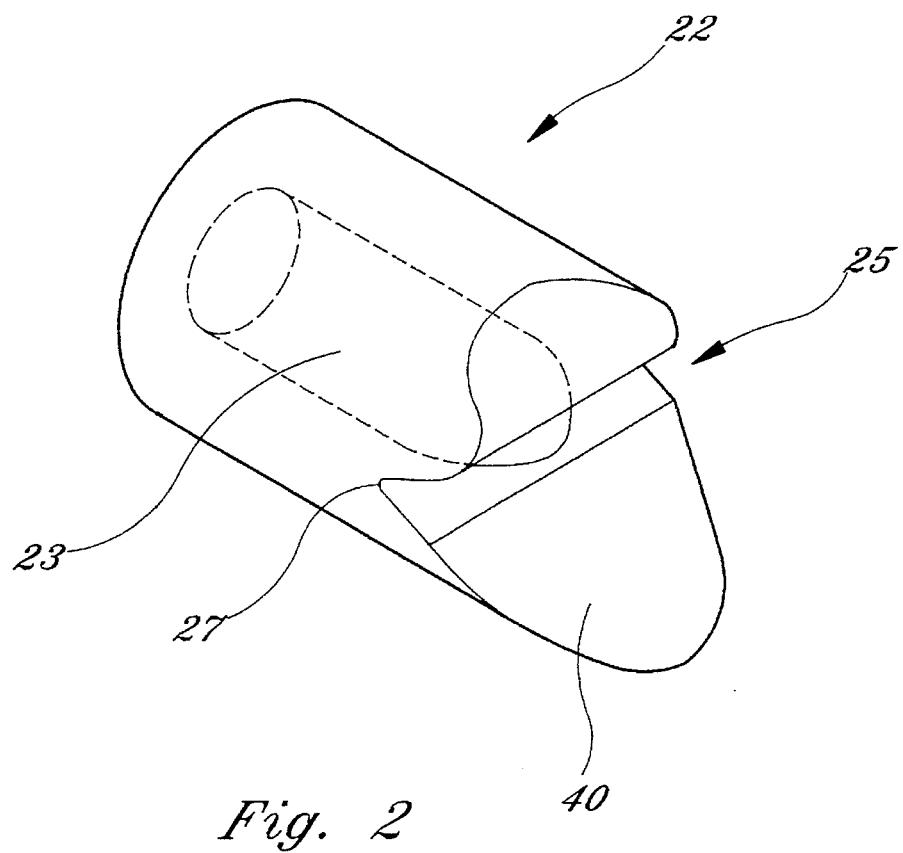
FIG. 2 is an enlarged isometric view of the operative end of the present invention.

As best seen in FIG. 2, the bottom half of the second end of operative member 22, can be provided with a dissecting edge 40. In one embodiment, edge 40 can be tapering. Edge 40 aids in pushing the various organs apart, as well as acting an instrument for dissecting and cutting with. However, edge 40 does not contribute to the flat wide, fan-like shape of the spray which shoots out of opening 25.

In operation, the surgical probe 10 is attached to a source of fluid, such as a trumpet valve, to provide fluid communication between the fluid source and internal passageways 13 and 23 of shaft 12 and operative member 22, respectively. Due to the V-shaped cutout 27 at opening 25, along with the relatively small size of the hole at the end of passageway 23, the fluid is forced through opening 25 in a flat wide fan-like shaped spray. The spray lifts the gall bladder from its sitting position on the liver bed. The adhesion disposed underneath the gall bladder is loosened by the spray and ultimately pulled out. Thus, the present invention provides an aid in defining and dissecting tissue planes.

Figure 4:
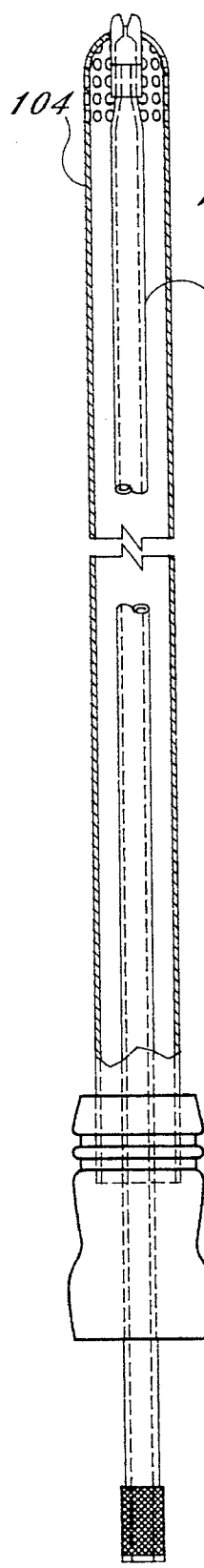
FIG. 4 is a side cutaway view showing the present invention used as the inner probe of a composite probe.
Figure 5:
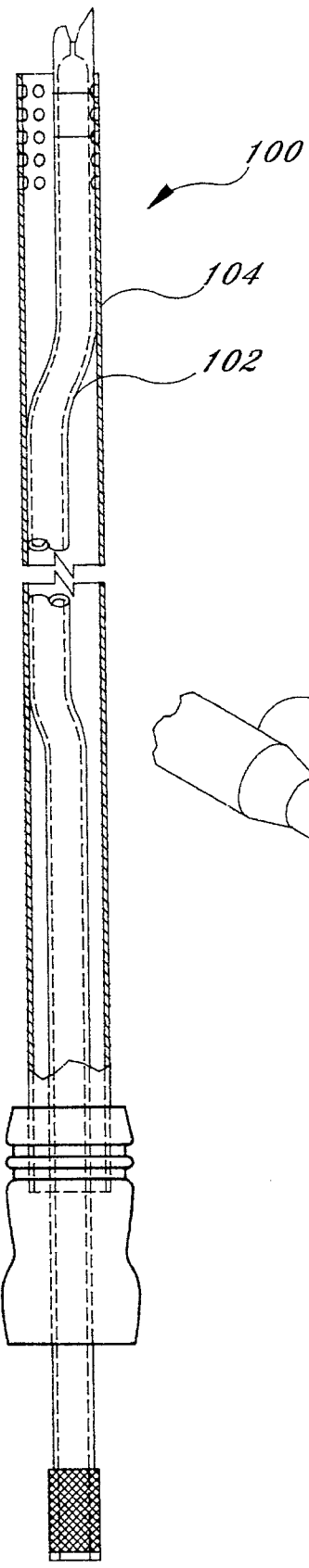
FIG. 5 is a side cutaway view showing the present invention used as the inner probe of a composite probe, with the inner probe having an offset.

As seen in FIG. 4 and 5, the present invention can be utilized as an inner probe cannula 102 in a composite probe 100. A composite probe 100 is the subject matter of my currently pending U.S. applicant Ser. No. 08/052,080, the subject matter of which is incorporated by reference herein. In this composite embodiment, inner probe cannula 102 is in a fixed relationship with respect to the outer probe cannula 104. As shown in U.S. application Ser. No. 08/052,080, inner cannula 102 can be straight (FIG. 4) or offset (FIG. 5) which allows debris to travel easier through outer cannula 104.

An alternative embodiment for the composite probe is my telescoping probe which allows the inner probe cannula to move relative to the outer probe cannula to allow the composite probe to be utilized in various surgical circumstances. The subject matter of the telescoping probe has also been filed with the United States Patent and Trademark Office and is currently pending. Such subject matter is also incorporated by reference herein.

Figure 6:
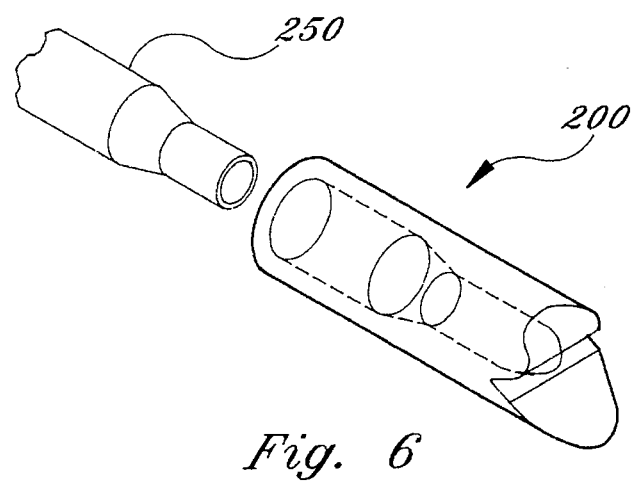
FIG. 6 is a perspective view showing the fan spray probe tip being used as an attachment to an existing probe.

Lastly, as seen in FIG. 6, the tip portion 200 of the present invention probe, which creates the flat fan shaped spray may be used as an attachment to conventional tip ends of an existing probe 250, to give such existing probes the capability of providing a flat fan shaped spray. The tip portion can be attached or fastened by any conventional means.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A surgical probe, comprising:

a probe shaft having a first end and a second end, said shaft defining an internal passageway extending from said first end to said second end;

means for providing a fan shaped irrigation spray, said means for providing forming the second end of said probe shaft; and means for attaching said probe shaft to a source of fluid.

2. The surgical probe of claim 1, wherein said means for attaching is a probe shaft housing having a first end adapted to be attached to the source of fluid and a second end encompassing a portion of the first end of said shaft.

3. The surgical probe of claim 1, wherein said means for providing is a V-shaped cutout at the second end of said probe shaft, the V-shaped cutout having an opening at a tip portion thereof, wherein the fluid travels through the internal passageway through said opening to provide, in conjunction with said V-shaped cutout, a flat wide fan spray at the second end of said probe shaft.

4. The surgical probe of claim 1, further comprising means for dissecting tissue planes between organs of a surgical patient, said means for dissecting disposed at the second end of said probe shaft.

5. A surgical probe, comprising:

a probe shaft having a first end and a second end, said shaft defining an internal passageway extending from said first end to said second end;

means for providing a fan shaped irrigation spray at said second end;

means for attaching said probe shaft to a source of fluid; and means for dissecting tissue planes between organs of a surgical patient, said means for dissecting being an edge extending outward from a bottom half of the second end of said probe shaft.

6. The surgical probe of claim 5, wherein said edge tapers outward from the second end of said probe shaft.

7. A surgical probe for aiding in defining and dissecting tissue planes, comprising:

a probe shaft having a first end and a second end, said shaft defining an internal passageway extending from said first end to said second;

a probe shaft housing having a first end adapted to be attached to a source of fluid and a second end encompassing a portion of the first end of said shaft; and means for providing a fan shaped spray, said means for providing forming the second end of said probe shaft.

8. The surgical probe of claim 7, wherein said means for providing is a V-shaped cutout at the second end of said probe shaft, the V-shaped cutout having an opening at a tip portion thereof, wherein the fluid travels through the internal passageway through said opening to provide, in conjunction with said V-shaped cutout, a flat wide fan spray at the second end of said probe shaft.

9. The surgical probe of claim 7, further comprising means for dissecting and/or cutting organs of a surgical patient.

10. The surgical probe of claim 7, further comprising means for cutting organs of a surgical patient.

11. The surgical probe of claim 7, further comprising means for dissecting and cutting organs of a surgical patient.

12. A surgical probe for aiding in defining and dissecting tissue planes, comprising:

a probe shaft having a first end and a second end, said shaft defining an internal passageway extending from said first end to said second;

a probe shaft housing having a first end adapted to be attached to a source of fluid and a second end encompassing a portion of the first end of said shaft;

means for providing a fan shaped spray at said second end of said probe shaft; and means for dissecting and/or cutting organs of a surgical patient, said means for dissecting being an edge extending outward from a bottom half of the second end of said probe shaft.

13. The surgical probe of claim 12, wherein said edge tapers outward from the second end of said probe shaft.

14. A surgical probe for aiding in defining and dissecting tissue planes during laparoscopic and endoscopic surgeries, comprising:

a probe shaft having a first end and a second end, said shaft defining an internal passageway extending from said first end to said second, said probe shaft having a V-shaped cutout, the V-shaped cutout having an opening at a tip portion thereof, said V-shaped cutout forming the second end of said probe shaft; and a probe shaft housing having a first end adapted to be attached to a source of fluid and a second end encompassing a portion of the first end of said shaft;

wherein fluid travels through the internal passageway through said opening to provide, in conjunction with said V-shaped cutout, a flat wide fan spray at the second end of said probe shaft.

15. The surgical probe of claim 14, further comprising means for dissecting organs of a surgical patient.

16. The surgical probe of claim 14, further comprising means for cutting organs of a surgical patient.

17. The surgical probe of claim 14, further comprising means for dissecting and cutting organs of a surgical patient.

18. A surgical probe for aiding in defining and dissecting tissue planes during laparoscopic and endoscopic surgeries, comprising:

a probe shaft having a first end and a second end, said shaft defining an internal passageway extending from said first end to said second, said probe shaft having a V-shaped cutout at the second end, the V-shaped cutout having an opening at a tip portion thereof;

a probe shaft housing having a first end adapted to be attached to a source of fluid and a second end encompassing a portion of the first end of said shaft;

wherein fluid travels through the internal passageway through said opening to provide, in conjunction with said V-shaped cutout, a flat wide fan spray at the second end of said probe shaft; and means for dissecting and cutting organs of a surgical patient, said means for dissecting being an edge extending outward from a bottom half of the second end of said probe shaft.

19. The surgical probe of claim 18, wherein said edge tapers outward from the second end of said probe shaft.

20. A composite surgical probe, comprising:

an outer probe shaft having a first end and a second end, said outer probe shaft defining an internal passageway extending from said first end to said second end;

an inner probe shaft having a first end and a second end, said inner probe shaft defining an internal passageway extending from said first end to said second end of said inner probe shaft, a substantial portion of said inner probe shaft being disposed within the internal passageway of said outer probe shaft;

means for providing a fan shaped irrigation spray, said means for providing forming the second end of said probe shaft; and means for attaching said composite probe to a source of fluid.

* * * * *